(12) United States Patent
Santangelo et al.

(10) Patent No.: US 9,816,954 B2
(45) Date of Patent: Nov. 14, 2017

(54) SENSOR OF VOLATILE SUBSTANCES AND PROCESS FOR MANUFACTURING A SENSOR OF VOLATILE SUBSTANCES

(71) Applicant: STMICROELECTRONICS S.R.L., Agrate Brianza (IT)

(72) Inventors: Antonello Santangelo, Belpasso (IT); Salvatore Cascino, Gravina di Catania (IT); Roberto Modica, Mascalucia (IT); Viviana Cerantonio, Acireale (IT); Maurizio Moschetti, Gravina di Catania (IT); Alessandro Auditore, Giarre (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 129 days.

(21) Appl. No.: 14/606,930

(22) Filed: Jan. 27, 2015

(65) Prior Publication Data

US 2015/0219581 A1 Aug. 6, 2015

(30) Foreign Application Priority Data

Jan. 31, 2014 (IT) .............. TO2014A0074

(51) Int. Cl.
*G01N 27/00* (2006.01)
*G01N 27/22* (2006.01)

(52) U.S. Cl.
CPC .......... *G01N 27/223* (2013.01); *G01N 27/00* (2013.01); *G01N 27/22* (2013.01); *G01N 27/227* (2013.01); *Y10T 29/43* (2015.01)

(58) Field of Classification Search
CPC ...... G01N 27/00; G01N 27/22; G01N 27/223; G01N 27/227

See application file for complete search history.

(56) References Cited

U.S. PATENT DOCUMENTS

| 5,296,819 A | 3/1994 | Kuroiwa et al. |
| 6,356,087 B1 | 3/2002 | Wallrafen |
| 6,690,569 B1 | 2/2004 | Mayer et al. |

(Continued)

FOREIGN PATENT DOCUMENTS

| DE | 3911812 A1 | 10/1990 |
| DE | 102 46 050 A1 | 4/2004 |
| EP | 1 387 164 A1 | 2/2004 |
| EP | 2 508 874 A1 | 10/2012 |

OTHER PUBLICATIONS

Gu et al., "A novel capacitive-type humidity sensor using CMOS fabrication technology," *Sensors and Actuators B* 99:491-498, 2004.

(Continued)

*Primary Examiner* — Hezron E Williams
*Assistant Examiner* — David Z Huang
(74) *Attorney, Agent, or Firm* — Seed IP Law Group LLP (57) ABSTRACT

A sensor of volatile substances includes: a first electrode structure and a second electrode structure capacitively coupled, comb-fingered, and arranged coplanar in a plane; and a sensitive layer, of a sensitive material that is permeable to a volatile substance and has electrical permittivity depending upon a concentration of the volatile substance absorbed by the sensitive material. The sensitive layer extends from opposite sides of the plane.

19 Claims, 8 Drawing Sheets

(56) References Cited

U.S. PATENT DOCUMENTS

| | | | |
|---|---|---|---|
| 9,164,052 B1 | 10/2015 | Speer et al. | |
| 2004/0080325 A1 | 4/2004 | Ogura | |
| 2009/0261845 A1* | 10/2009 | Hierlemann | G01N 27/227 324/658 |
| 2010/0134948 A1* | 6/2010 | Park | G01N 27/223 361/286 |
| 2010/0147070 A1 | 6/2010 | Jun et al. | |
| 2012/0304742 A1* | 12/2012 | Cummins | G01N 27/121 73/31.06 |
| 2013/0049212 A1* | 2/2013 | Hata | G01C 19/5762 257/773 |
| 2013/0187670 A1 | 7/2013 | Dooley et al. | |
| 2014/0077314 A1* | 3/2014 | Humbert | G01N 27/227 257/414 |
| 2014/0139241 A1* | 5/2014 | Sakai | G01N 27/223 324/665 |

OTHER PUBLICATIONS

Kang et al., "A High-Speed Capacitive Humidity Sensor with On-Chip Thermal Reset," *IEEE Transactions on Electron Devices* 47(4):702-710, Apr. 2000.

Kim et al., "High Sensitivity Capacitive Humidity Sensor with a Novel Polyimide Design Fabricated by MEMS Technology," Proceedings of the 2009 4th IEEE International Conference on Nano/Micro Engineered and Molecular Systems, Jan. 5-8, 2009, Shenzhen, China, pp. 703-706.

Laconte et al., "Capacitive Humidity Sensor Using a Polyimide Sensing Film," 2003 Design, Test, Integration & Packaging of MEMS/MOEMS, Cannes-Mandelieu, France, May 5-7, 2003, pp. 223-228.

Melcher et al., "Dielectric Effects of Moisture in Polyimide," *IEEE Transactions on Electrical Insulation* 24(1):31-38, Feb. 1989.

Patel et al., "Chemicapacitive microsensors for detection of explosives and TICs," *SPIE* 5986-22 2:1-10, Aug. 29, 2005.

Saikumar et al., "Time Lag and Permeation in Multilayer Polymer Coatings," *IEEE Transactions on Components, Hybrids, and Manufacturing Technology* 16(5):517-522, Aug. 1993.

Schubert et al., "A Polyimide-Based Capacitive Humidity Sensor," *IEEE Transactions on Electron Devices* ED-32(7):1220-1223, Jul. 1985.

Wang et al., "A Low-Cost Capacitive Relative Humidity Sensor for Food Moisture Monitoring Application," Proceedings of the 4th Asia Symposium on Quality Electronic Design, Jul. 10-11, 2012, Penang, Malaysia, pp. 95-99.

Zeng et al., "Fabrication and Test of MEMS/NEMS based Polyimide Integrated Humidity, Temperature and Pressure Sensor," Proceedings of the 1st IEEE International Conference on Nano/Micro Engineered and Molecular Systems, Jan. 18-21, 2006, Zhuhai, China, pp. 788-791.

Zhao et al., "A Fully Packaged CMOS Interdigital Capacitive Humidity Sensor With Polysilicon Heaters," *IEEE Sensors Journal* 11(11):2986-2992, Nov. 2011.

* cited by examiner

FIG. 19

SENSOR OF VOLATILE SUBSTANCES AND PROCESS FOR MANUFACTURING A SENSOR OF VOLATILE SUBSTANCES

BACKGROUND

Technical Field

The present disclosure relates to a sensor of volatile substances and to a process for manufacturing a sensor of volatile substances.

Description of the Related Art

Known to the art are humidity sensors of a capacitive type, which exploit as sensitive materials particular hygroscopic dielectric materials having an electrical permittivity that varies as a function of the degree of relative humidity. In practice, a sensitive layer of hygroscopic dielectric material is set between conductive structures coupled for forming the electrodes of a capacitor. The capacitance of the capacitor notoriously depends upon the electrical permittivity of the material that is set between the electrodes. Since this varies according to the humidity absorbed by the sensitive layer, the reading of the capacitance of the capacitor provides a measurement of the level of relative humidity in the environment.

Capacitive humidity sensors are much appreciated owing to their high sensitivity, good linearity over a wide range of values of relative humidity, low consumption, ease of miniaturization, and low manufacturing costs.

Some known types of capacitive humidity sensors use capacitors with plane and parallel plates. In this case, the electrodes of the capacitor are defined by parallel plates, and the sensitive layer is contained in a volume comprised between the electrodes. One of the electrodes of the capacitor, an external one, has through openings for enabling the environmental humidity to impregnate the sensitive layer. A limit of sensors of this type is represented by the rather slow response times. In fact, the exposed surface of the sensitive layer is small and is limited to the areas corresponding to the openings of the external electrode, which, on the other hand, cannot be increased beyond a certain limit without affecting the overall capacitance of the sensor.

Also sensors based upon comb-fingered capacitive structures have been proposed. In this case, two comb-shaped, coplanar and interdigitated electrodes are provided on a planar dielectric substrate and then coated with a sensitive layer of hygroscopic dielectric material, the electrical permittivity of which varies as a function of the humidity absorbed.

Sensors of this type have better response times as compared to sensors with plane and parallel plates, but the sensitivity is not very high because the portion of the sensitive layer capable of affecting the overall capacitance of the sensor is of small extent.

It would, instead, be desirable to have available capacitive sensors with a ready response, like sensors based upon comb-fingered electrodes, but with a higher sensitivity.

BRIEF SUMMARY

The present disclosure is directed to a sensor of volatile substances and a process for manufacturing a sensor of volatile substances that overcomes the limitations described above and, in particular, enables increase in the sensitivity as compared to known comb-fingered structures, without jeopardizing the response times.

One embodiment of the present disclosure is directed to a sensor of volatile substances that includes a first electrode structure and a second electrode structure capacitively coupled, comb-fingered and arranged co-planar on a plane and a sensitive layer, of a sensitive material that is permeable to a volatile substance and has electric permittivity dependent on a concentration of the volatile substance absorbed by the sensitive material, the sensitive layer extending on opposite sides of the plane.

BRIEF DESCRIPTION OF THE SEVERAL VIEWS OF THE DRAWINGS

For a better understanding of the disclosure, some embodiments thereof will now be described, purely by way of non-limiting example and with reference to the attached drawings, wherein.

DETAILED DESCRIPTION

Figure 1:
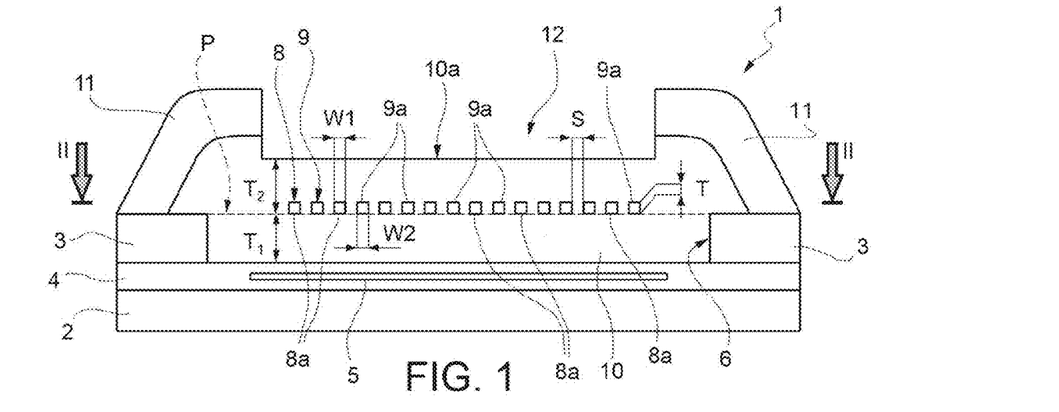
FIG. 1 is a cross-section through a sensor of volatile substances according to one embodiment of the present disclosure.
Figure 2:
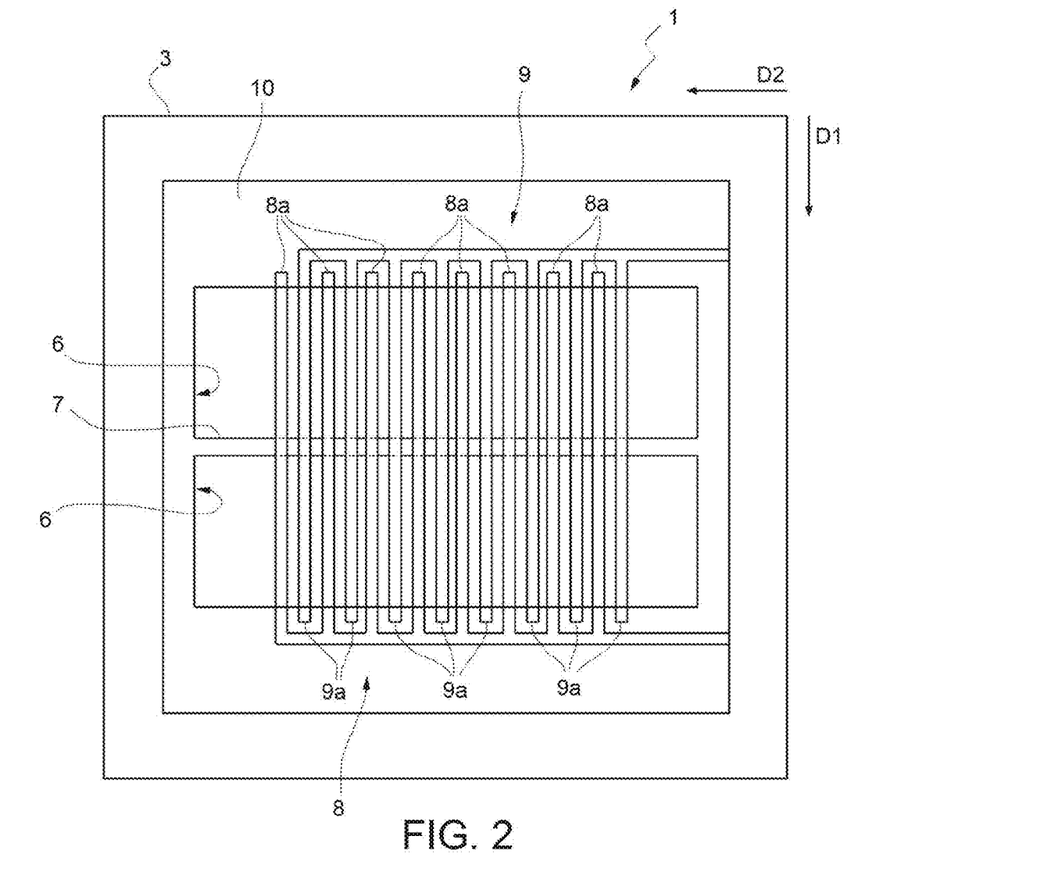
FIG. 2 is a top plan view of the sensor of FIG. 1, sectioned along the plane II-II of FIG. 1.

With reference to FIGS. 1 and 2, a sensor of volatile substances, in the case in point a humidity sensor, is designated as a whole by the number 1.

The sensor of volatile substances 1 is of a capacitive type and uses as sensitive material a hygroscopic polymer the electrical permittivity of which varies as a function of the humidity absorbed.

In detail, the sensor of volatile substances 1 comprises a substrate 2, for example of silicon, provided on which is a structural layer 3 of dielectric material, for example silicon oxide. In one embodiment, present between the substrate 2 and the structural layer 3 is a dielectric layer 4 incorporating a heater 5. In other embodiments, the dielectric layer 4 and the heater may be absent, or else the heater 5 may be made directly on the substrate 2.

The substrate 2 and the dielectric layer 4 define a supporting layer for the structural layer 3 and the other structures described hereinafter.

The structural layer 3 has one or more cavities 6 in a region corresponding to the heater 5. In the embodiment described, two cavities 6 are present aligned and separated by a supporting wall 7 (FIG. 2). Furthermore, the cavities 6 traverse the entire structural layer 3. Consequently, the bottom 6a is defined by a surface of the underlying layer, which in this case is the dielectric layer 4.

A first electrode structure 8 and a second electrode structure 9, which are coplanar, are provided in a plane P defined by a surface of the structural layer 3 opposite to the substrate 2 (FIG. 1). The first electrode structure 8 and the second electrode structure 9 are defined by comb-fingered conductive strips. More precisely (FIG. 2), the first electrode structure 8 and the second electrode structure 9 comprise respective teeth 8a, 9a that extend in a first direction D1 and are arranged to bridge the cavities 6, in a direction transverse to the supporting wall 7. The teeth 8a, 9a are further arranged alternated in succession in a second direction D2 perpendicular to the first direction D1. Adjacent teeth 8a, 9a are separated by a uniform spacing S. Furthermore, the teeth 8a, 9a have the same thickness T and respective widths W1, W2 in the second direction D2. In one embodiment, the spacing S, the thickness T, and the widths W1, W2 of the teeth 8a, 9a are the same as one another and are less than 1 µm, for example 0.1 µm. In other embodiments, however, the widths W1, W2 of the teeth 8a, 9a may be different from one another and different from the thickness T and from the spacing S. In addition, the spacing S may not be uniform.

In one embodiment, the first electrode structure 8 and the second electrode structure 9 are made of a refractory conductive material, for example an alloy of tantalum and aluminum substantially in equal parts. Alternatively, corrosion-resistant metals may be used, such as gold or platinum, or else again copper or aluminum. Refractory alloys and corrosion-resistant metals present the advantage of not being damaged by the presence of humidity. In the other cases, the electrode structures 8, 9 may be coated with a protective layer (not shown).

The teeth 8a, 9a of the first electrode structure 8 and of the second electrode structure 9, respectively, are incorporated in a sensitive layer 10 that fills the cavities 6 and projects from the plane P. The sensitive material is a material permeable to a volatile substance to be detected and has an electrical permittivity that depends upon the concentration of the volatile substance absorbed by the sensitive material itself. For instance, the electrical permittivity of the sensitive material increases as the concentration of the volatile substance absorbed increases. In one embodiment, the sensitive material is a hygroscopic polymeric material, in particular polyimide (PI), and the sensor 1 is a humidity sensor. In this case, in particular, the electrical permittivity increases as the humidity absorbed by the sensitive material increases.

As an alternative different sensitive materials may be used for detecting other non-volatile substances. Table 1 presents a non-exhaustive list of sensitive materials, in particular polymers, that may be used instead of polyimide, and of the substances that may be detected by said sensitive materials.

TABLE 1

| MATERIAL OF SENSITIVE LAYER | SUBSTANCES DETECTED |
| --- | --- |
| PMMA<br>polymethyl methacrylate | Toluene,<br>Chloroform,<br>Non-polar hydrocarbons |
| PHEMA<br>poly(2-hydroxymethyl methacrylate) | Water,<br>Methanol,<br>Ethanol |
| Photopatternable PDMS<br>94.5% polydimethyl siloxane copolymer<br>5% diphenyl siloxane copolymer<br>0.5% methylvinyl siloxane | Toluene,<br>Chloroform,<br>Non-polar hydrocarbons |
| PEVA 40%<br>polyethylene-covinyl acetate with<br>40% of acetate content | Aromatic low-polarity<br>hydrocarbons |
| PCUT<br>polycarbonate urethane | Low-polarity hydrocarbons |
| Dicyanoallyl-silicone | Nitroalkanes,<br>Polar volatile organic<br>compounds |
| SXFA<br>siloxane-hexafluoro alcohol | Polar volatile organic<br>compounds, Hydrogen-<br>binding bases |

The sensitive layer 10 extends from the plane P wherein the electrode structures 8, 9 lie, on one side as far as the bottom 6a of the cavities 6 and on the other side as far as a free surface 10a exposed to the air so that the teeth 8a, 9a will be entirely englobed in the sensitive layer 10. Advantageously, the portions of the sensitive layer 10 comprised between the plane P and the bottom 6a of the cavities 6 and between the plane P and the free surface 10a have respective thicknesses T1, T2 approximately equal to the sum of the width W of one of the teeth 8a, 9a and of the spacing S or greater. The thicknesses T1, T2 may or may not be the same as one another.

The sensor 1 is coated with a passivation layer 11, which has a window 12 for access to the sensitive layer 10. The window 12 leaves the free surface 10a exposed and accessible so that the environmental humidity (or the other substances to be detected) may impregnate the sensitive layer 10, modifying its electrical permittivity.

In the sensor 1, the portions of the electrode structures 8, 9 that are capacitively coupled are completely incorporated in the sensitive layer 10. In other words, the region that surrounds the electrode structures 8, 9 and that determines the overall capacitance of the sensor 1 and its variations is entirely occupied by sensitive material.

Instead, in known sensors approximately half of this region is occupied by a dielectric, the electrical permittivity of which is not affected by absorption of volatile substances and thus does not supply any detectable contribution. In practice, from the electrical standpoint known sensors may be schematically represented as the parallel of two capacitors, just one of which, however, has a variable capacitance. The sensor 1 is equivalent, instead, to a single capacitor with variable capacitance, with negligible parasitic contributions.

Given the same dimensions and variations of concentration of the volatile substances absorbed, the variations of capacitance of the sensor 1 are thus greater and its sensitivity is improved. Conversely, given the same sensitivity, the dimensions of the sensor 1 may be reduced.

With the dimensions indicated, furthermore, the sensitive material is substantially confined within the region that affects the capacitance of the sensor 1. The response times are thus short, since the volatile substances to be detected do not have to impregnate thicknesses of sensitive material that, in effect, would be at an excessive distance from the electrode structures 8, 9 to affect the capacitance of the sensor 1 appreciably.

FIGS. 3-6 illustrate a process for manufacturing the sensor 1.

Initially (FIG. 3), the dielectric layer 4 and the heater incorporated therein are made on the substrate 2 of a semiconductor wafer 50. For instance, a first thickness of dielectric material is deposited or grown thermally on the substrate 2 and then coated with a layer of conductive material, which could be polycrystalline silicon, and which is defined with a photolithographic process for providing the heater 5. A second thickness of dielectric material may optionally be then deposited for incorporating the heater 5.

Figure 3:
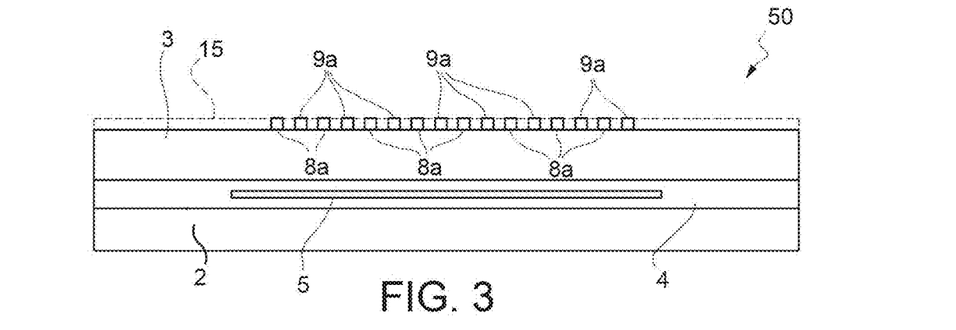
FIG. 3 shows a cross-section of a semiconductor wafer after initial steps of a process for manufacturing a sensor of volatile substances according to one embodiment of the present disclosure.

The structural layer 3 and a conductive layer 15 of 50%-50% tantalum and aluminum alloy are formed in succession on the supporting body, which in the example of FIG. 3 is formed by the substrate 2 and by the dielectric layer 4. The conductive layer 15 may be conveniently obtained by sputtering.

The first electrode structure 8 and the second electrode structure 9 are then obtained from the conductive layer 15 by a further photolithographic process. The structural layer 3 has a thickness at least equal to the sum of the width of one of the teeth 8a, 9a and of the spacing S.

Figure 4:
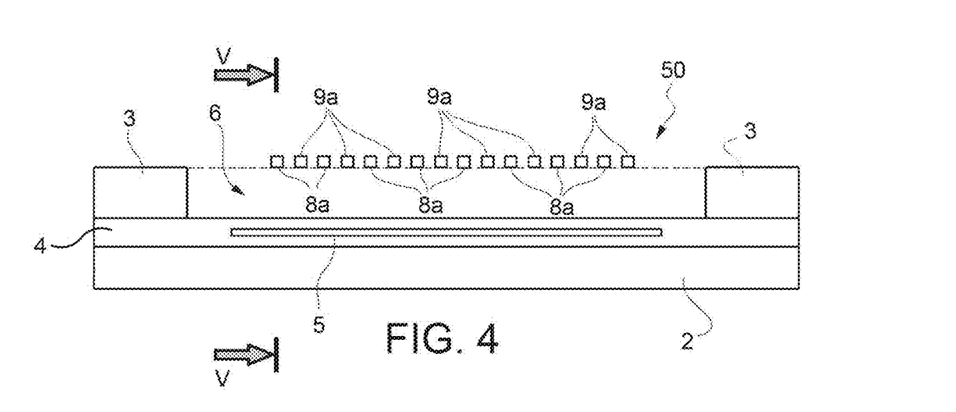
FIG. 4 shows a cross-section of the wafer of FIG. 3 in a subsequent step of the manufacturing process.
Figure 5:
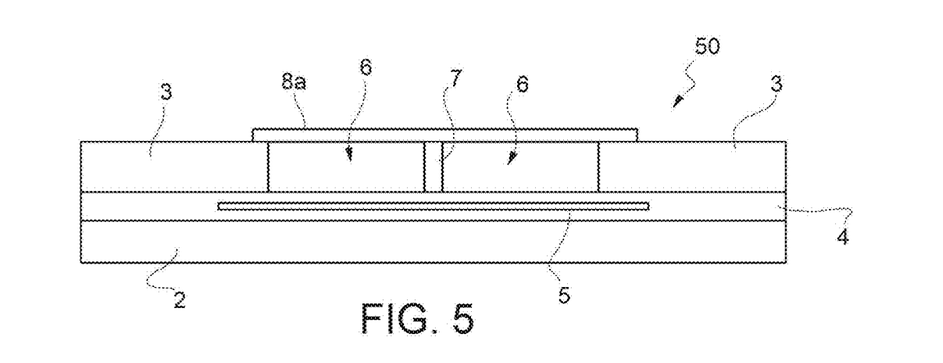
FIG. 5 shows a cross-section of the wafer of FIG. 4, taken along the plane V-V of FIG. 4.

Next, the structural layer 3 is etched to form the cavities 6 in a region underlying the electrode structures 8, 9, as shown in FIGS. 4 and 5. The shape of the surfaces that delimit the cavities 6 is not critical and the etch may be made in different ways. For instance, a substantially isotropic wet etch or else an anisotropic dry etch may be made. Furthermore, if the material of the dielectric layer 4 (for example, silicon nitride) enables a sufficient selectivity with respect to the material of the structural layer 3 (here silicon oxide), the etch may be a through etch and the dielectric layer 4 may be used as stopper layer; otherwise, the etch may be a time-controlled etch.

In addition, the number of cavities 6 and of corresponding supporting walls 7 may be different according to the dimensions of the teeth 8a, 9a of the electrode structures 8, 9 and to offer support prior to filling with the sensitive material. In some cases, a single cavity 6 without supporting walls may be present.

At the end of the etch, the electrode structures 8, 9 are suspended over the cavities 6, have respective ends anchored to the structural layer 3, and are supported at the center by the wall 7.

Figure 6:
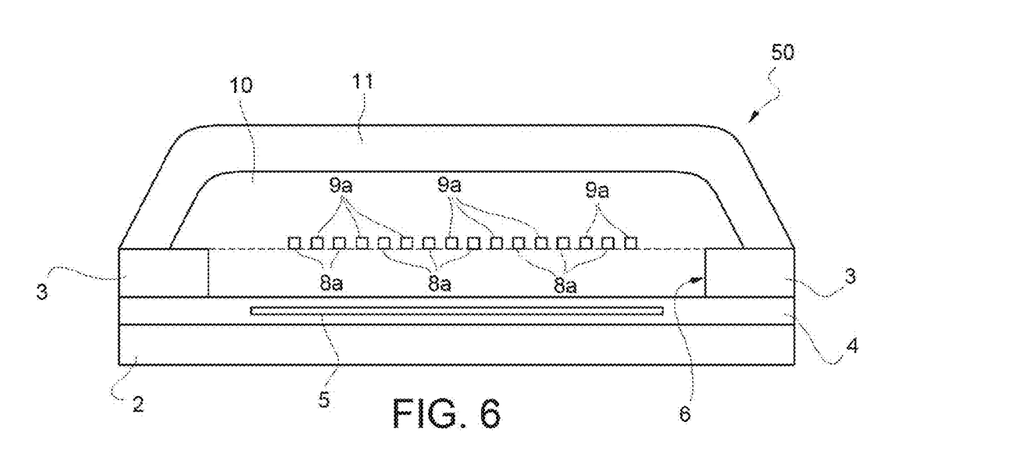
FIG. 6 shows a cross-section of the wafer of FIG. 3 in a subsequent step of the manufacturing process.

The cavities 6 are then filled with the sensitive material, and the sensitive layer 10 is formed, as shown in FIG. 6. After the sensitive layer 10 has been deposited, it is exposed to light, if necessary, and subjected to a curing step.

The passivation layer 11 is then deposited, and the window 12 is opened, thus also defining the surface 10a of the sensitive layer 10. The wafer 50 is finally diced, and the structure of FIGS. 1 and 2 is thus obtained.

According to a different embodiment of the process (illustrated in FIGS. 7-10), a dielectric layer 104 is initially formed on a substrate 102 of a semiconductor wafer 150. A heater 105 is formed on the dielectric layer 104, without then being incorporated therein.

Figure 7:
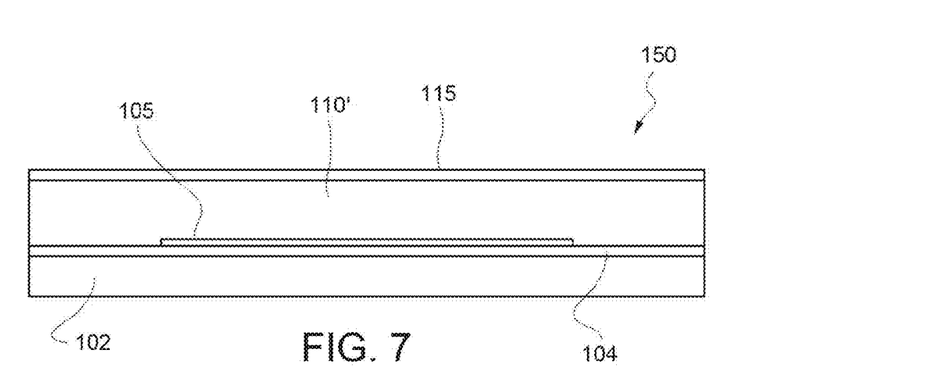
FIGS. 7 and 8 show cross-sections through a semiconductor wafer in subsequent steps of a process for manufacturing a sensor of volatile substances according to a different embodiment of the present disclosure.

A first portion of sensitive layer 110' of a sensitive material and a conductive layer 115 are then deposited on the dielectric layer 104. The sensitive material is a material permeable to a volatile substance to be detected and has electrical permittivity that depends upon the concentration of the volatile substance absorbed by the sensitive material itself.

Figure 8:
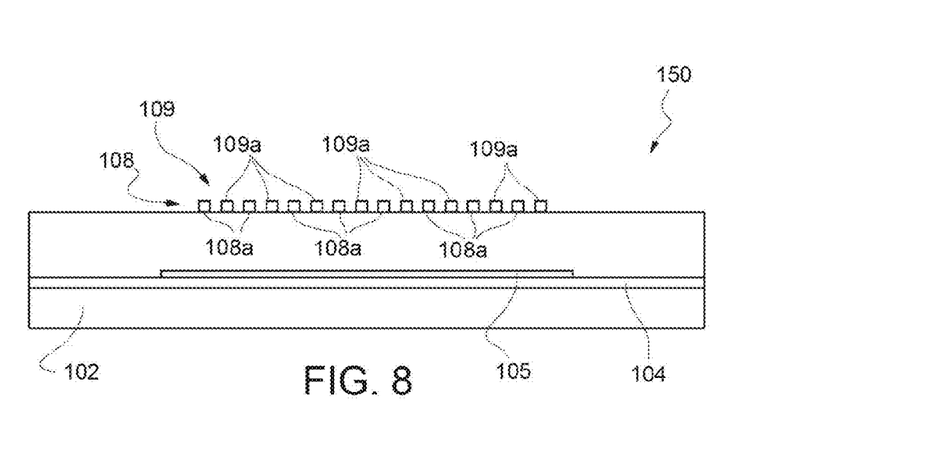
Figure 9:
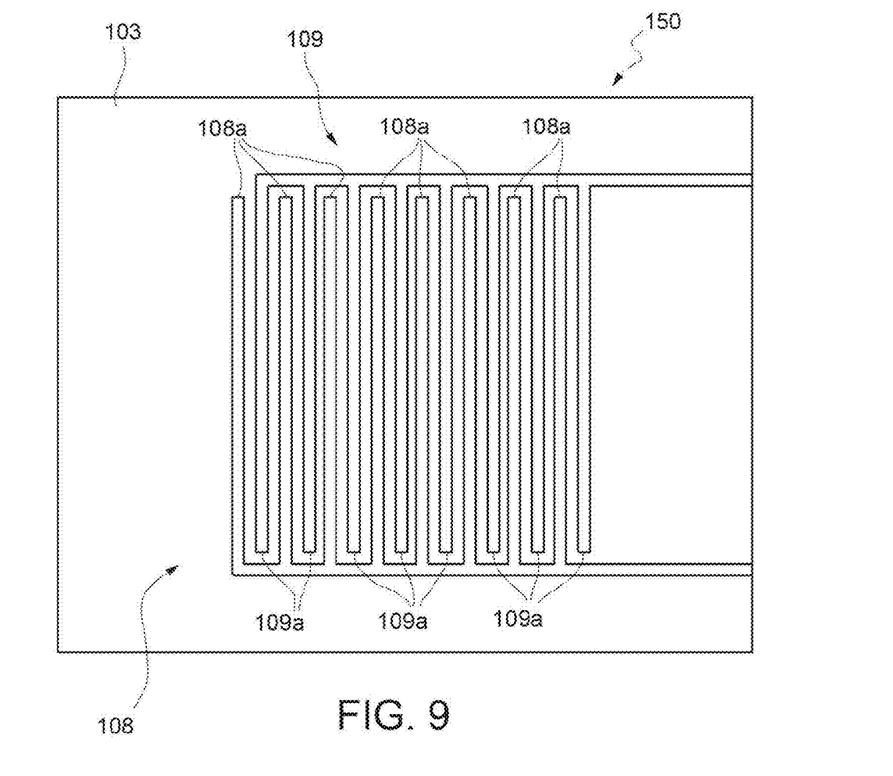
FIG. 9 shows a top plan view of the wafer of FIG. 8.

The conductive layer 115 is patterned to form a first electrode structure 108 and a second electrode structure 109 which are comb-fingered, as shown in FIGS. 8 and 9.

Then (FIG. 10), a second portion of sensitive layer 110" and a passivation layer 111 are formed in sequence on the first portion of sensitive layer 110'. In this way, the first portion of sensitive layer 110' and the second portion of sensitive layer 110" form a single sensitive layer 110 that extends between a surface 104a of the dielectric layer 104 and a free surface 110a opposite to the surface 104a with respect to the plane in which the first electrode structure 108 and the second electrode structure 109 are arranged. The sensitive layer 110 consequently incorporates the first electrode structure 108 and the second electrode structure 109.

Figure 10:
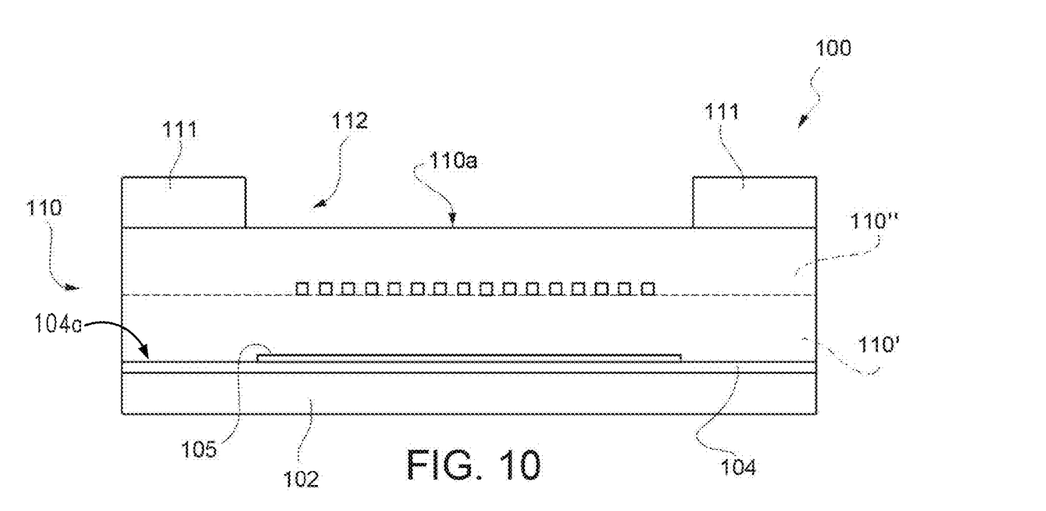
FIG. 10 is a cross-section through a sensor of volatile substances according to a different embodiment of the present disclosure.

The free surface 110a is exposed to the air to enable absorption of the volatile substance to be detected.

The sensitive layer 110 is then exposed to light and undergoes curing.

In the passivation layer 111, a window 112 is then opened to enable the sensitive layer 110 to absorb the volatile substance to be detected, and the wafer 150 is diced. The sensor of volatile substances 100 illustrated in FIG. 10 is thus obtained.

Figure 11:
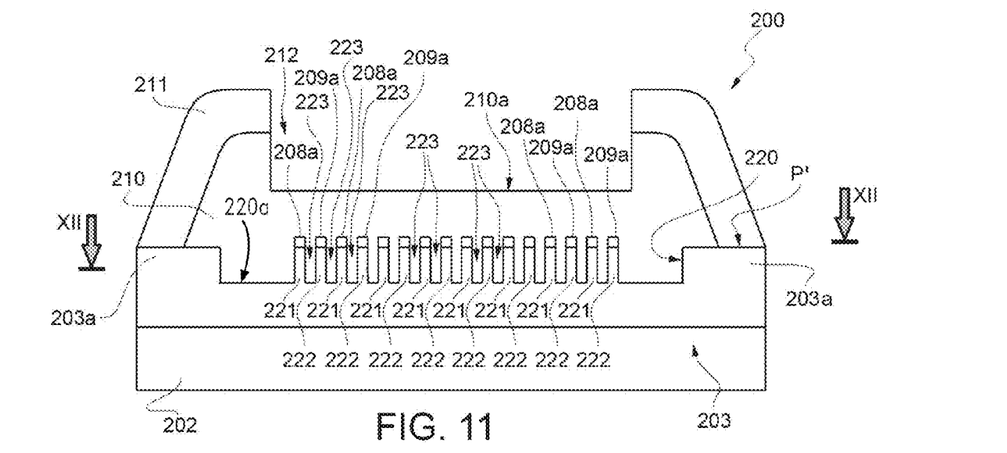
FIG. 11 is a cross-section through a sensor of volatile substances according to a further embodiment of the present disclosure.
Figure 12:
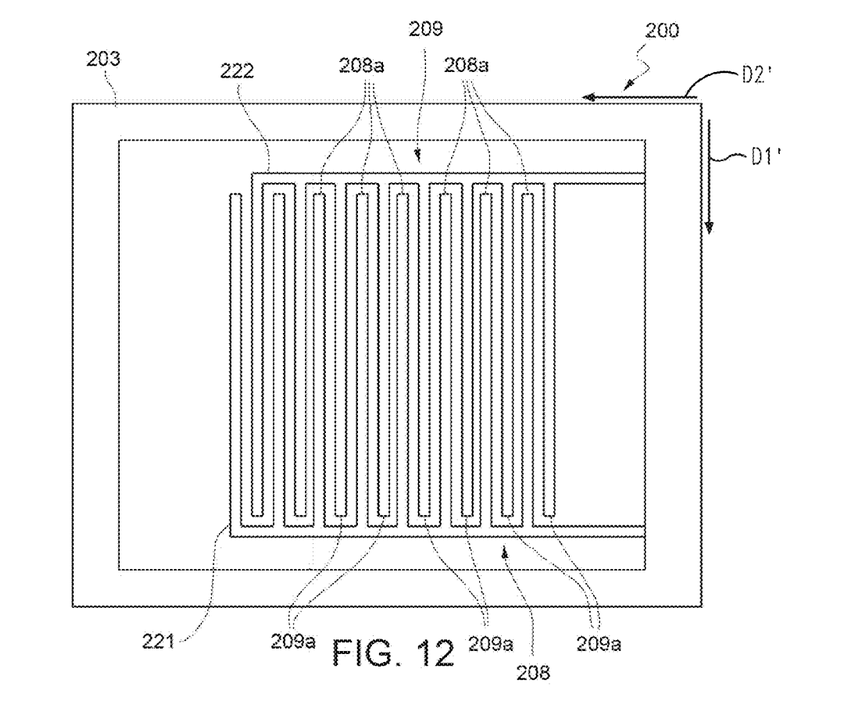
FIG. 12 is a top plan view of the sensor of FIG. 11, sectioned along the plane XII-XII of FIG. 11.

FIGS. 11 and 12 show a sensor of volatile substances 200 according to a different embodiment of the disclosure. The sensor 200 comprises a substrate 202, a structural layer 203 of dielectric material on the substrate 202, a first electrode structure 208, a second electrode structure 209, and a sensitive layer 210 of a sensitive material. The sensitive material is a material permeable to a volatile substance to be detected and has electrical permittivity that depends upon the concentration of the volatile substance absorbed by the sensitive material itself.

The first electrode structure 208 and the second electrode structure 209 are arranged in a plane P' defined by a surface of the structural layer 203 opposite to the substrate 202 and comprise comb-fingered conductive strips. More precisely, the first electrode structure 208 and the second electrode structure 209 comprise respective teeth 208a, 209a that extend in a first direction D1'. The teeth 208a, 209a are further set alternated in succession in a second direction D2' perpendicular to the first direction D1'. Adjacent teeth 208a, 209a are separated by a uniform spacing. In addition, the teeth 208a, 209a have the same thickness and the same width in the second direction D2'.

The first electrode structure 208 and the second electrode structure 209 are supported by the structural layer 203. In greater detail, the structural layer 203 comprises an outer frame 203a, which delimits a cavity 220, and a first supporting structure 221 and a second supporting structure 222 in the cavity 220. The first supporting structure 221 and the second supporting structure 222 project from a bottom surface 220a of the cavity 220 up to a surface of the structural layer 203 opposite to the substrate 202 and support the first electrode structure 208 and the second electrode structure 209, respectively. Furthermore, the first supporting structure 221 and the second supporting structure 222 are defined by walls that extend substantially perpendicular to the surface defining the plane P' along the path of the first electrode structure 208 and along the path of the second electrode structure 209, respectively. In plan view, i.e., from a direction perpendicular to the plane P', the first supporting structure 221 has the same shape as the first electrode structure 208, and the second supporting structure 222 has the same shape as the second electrode structure 209.

The first supporting structure 221 and the second supporting structure 222 define between them a labyrinthine recess 223 that extends from the bottom surface 220a of the cavity 220 up to the surface of the structural layer 203 that defines the plane P'.

The sensitive layer 210 fills the cavity 220 and the labyrinthine recess 223 and projects out of them. The sensitive layer 210 thus extends over both of the sides of the plane P', precisely between the plane P' and the bottom surface of the cavity 220 and of the labyrinthine recesses 223 and between the plane P' and a free surface 210a.

The sensor 200 is finally coated with a passivation layer 211, which has a window 212 for access to the sensitive layer 210. The window 212 leaves the free surface 210a exposed and accessible so that the substance or substances to be detected may impregnate the sensitive layer 210, modifying its electrical permittivity.

Also in this case, the sensitive material substantially occupies the entire region of space where the presence of dielectric provides a significant contribution to the capacitance between the first electrode structure 208 and the second electrode structure 209. In fact, given that the first electrode structure 208 and the second electrode structure 209 are coplanar and set alongside one another, the portions of dielectric having an electrical permittivity independent of the absorption of volatile substances (which occupy the regions underlying the electrode structures 208, 209) have practically no effect as regards the overall capacitance of the sensor 200. Thus, once more, the entire dielectric significantly involved in the electrical field set up between the electrode structures 208, 209 is sensitive material, whereas the contribution of the parasitic capacitances is marginal (where by "parasitic capacitances" is meant the capacitive contributions corresponding to regions occupied by dielectric with constant electrical permittivity in regard to absorption of volatile substances). The sensitivity, given the same dimensions, is in any case improved as compared to known devices. Conversely, given the same sensitivity, the dimensions of the sensor 200 may advantageously be reduced.

The frame 203a advantageously enables housing of connection lines and contact pads (not shown) in the same plane P' as that of the electrode structures 208, 209. The manufacturing process is generally simplified, because it is as a rule easier to provide planar structures. Furthermore, some procedures such as planarization steps, may be used, if need be, which is not possible in the presence of projecting structures that are preserved.

Figure 13:
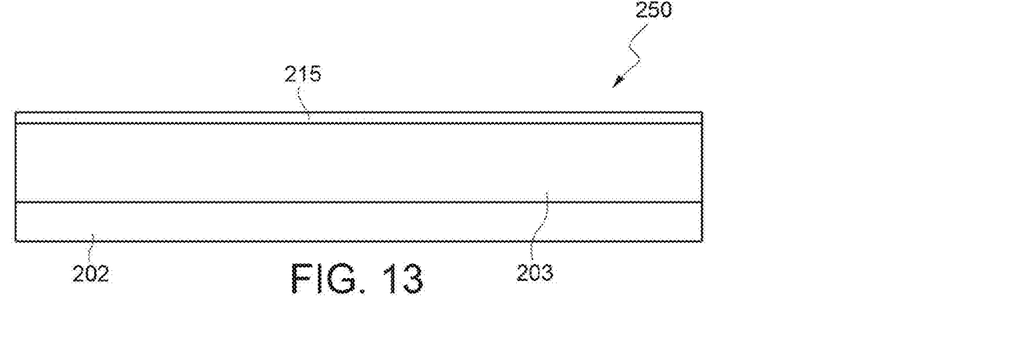
FIGS. 13-15 are cross-sections through a semiconductor wafer in subsequent steps of a process for manufacturing a sensor of volatile substances according to a further embodiment of the present disclosure.
Figure 14:
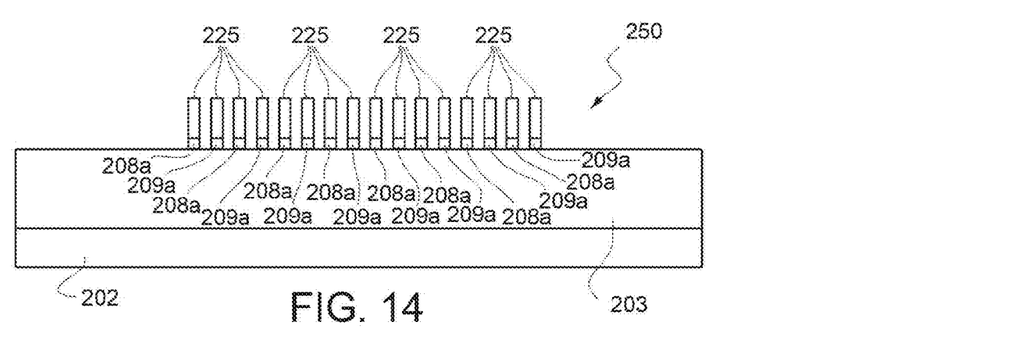
Figure 15:
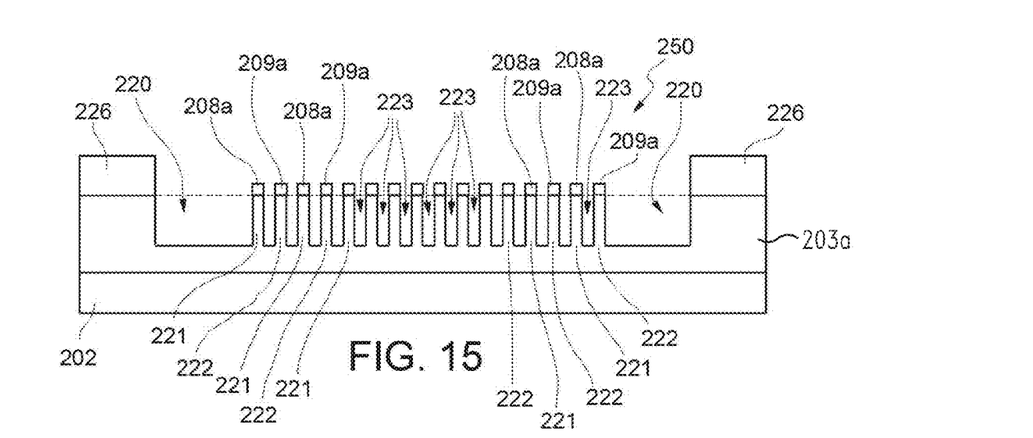

FIGS. 13-15 illustrate a process for manufacturing the sensor 200.

Initially, the structural layer 203, for example silicon oxide, is formed on the substrate 202 in a semiconductor wafer 250, and a conductive layer 215 is then formed, for example made of a 50%-50% tantalum and aluminum alloy, which coats the structural layer 203.

Then (FIG. 14), a first resist mask 225 is formed and used for defining the conductive layer 215 and obtaining the first electrode structure 208 and the second electrode structure 209.

The first resist mask 225 is removed as shown in FIG. 15, and a second resist mask 226 is formed, which coats a region corresponding to the frame 203a. The structural layer 203 is etched using the second resist mask 226 and the electrode structures 208, 209 as patterning structures. A cavity 220 and the labyrinthine recess 223 are thus opened.

There are then deposited in succession the sensitive layer 210, which is exposed to light and cured, and the passivation layer 211, and the window 212 is opened. Finally, the wafer 250 is diced, thus obtaining the sensor 200 illustrated in FIG. 11.

Figure 16:
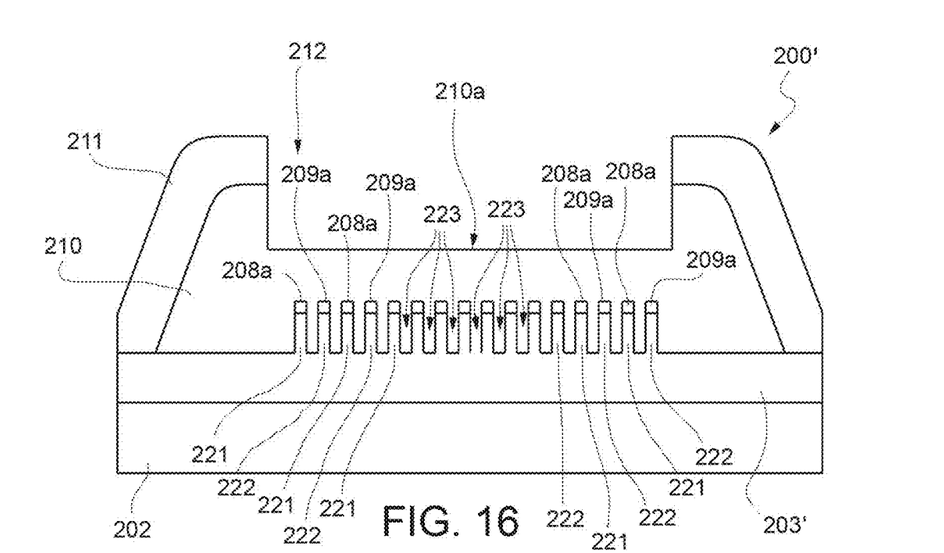
FIG. 16 is a cross-section through a sensor of volatile substances according to a further embodiment of the present disclosure.

According to a variant of the process, a single resist mask is used for etching both the conductive layer 215 and the structural layer, designated by 203' in FIG. 16. In this case, the entire portion of the structural layer 203' is removed around the supporting structures 221, 222 so that at the end of this step the structural layer 203' is without any frame, and the sensor of volatile substances 200' shown in FIG. 16 is obtained.

Figure 17:
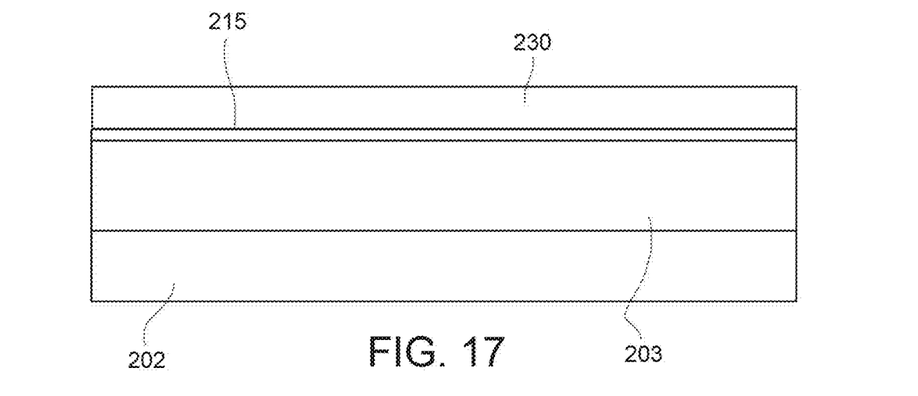
FIGS. 17-19 are cross-sections through a semiconductor wafer in subsequent steps of a process for manufacturing a sensor of volatile substances according to yet a further embodiment of the present disclosure.
Figure 18:
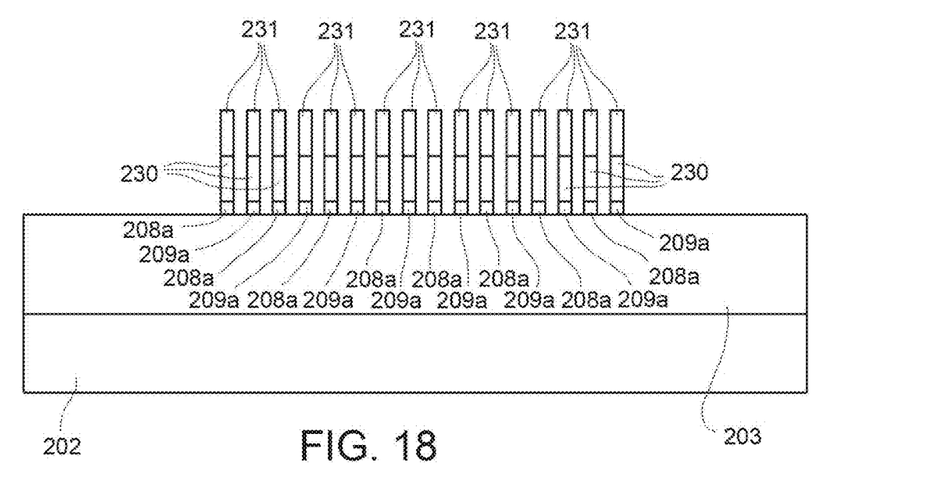
Figure 19:
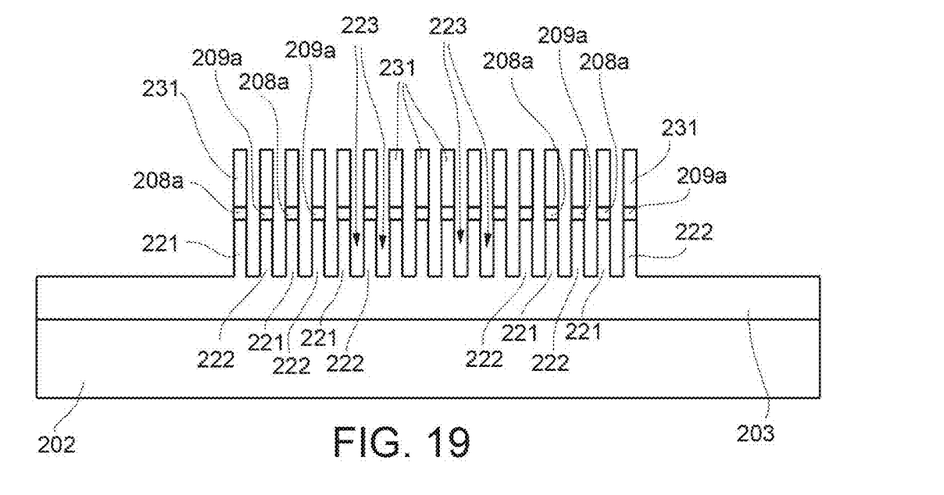

The same structure may be obtained by a further variant of the process, illustrated in FIGS. 17-19.

In this case (FIG. 17), after the structural layer 203 and the conductive layer 215 have been made on the substrate 202 (by thermal oxidation and sputtering, respectively), a metallization layer 230 is formed.

The metallization layer 230 and the conductive layer 215 are patterned using a resist mask 231 to form the electrode structures 208, 209, as shown in FIG. 18. From the metallization layer 230 conductive lines and contact pads (not shown) are obtained for connection of the sensor to external devices, such as a control unit.

Then, a dry etch of the structural layer 203 is carried out to form the supporting structures 221, 222 (FIG. 19). The residual portions of the metallization layer 230 protect the electrode structures 221, 222 during etching of the structural layer 203.

After parts of the metallization layer 230 necessary for operation and connection of the sensor (not shown) have been protected, the residual portions of the metallization layer are removed, in particular above the electrode structures 208, 209. The process then proceeds with deposition, exposure to light, and curing of the sensitive layer 210, with deposition of the passivation layer 211, and with opening of the window 212, to obtain the structure of FIG. 16.

Finally, it is evident that modifications and variations may be made to the sensor and to the process described herein, without thereby departing from the scope of the present disclosure.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A sensor of substances, comprising:
   a first electrode structure and a second electrode structure capacitively coupled, comb-fingered and arranged coplanar on a plane;
   a sensitive layer, of a sensitive material that is permeable to a substance and has electric permittivity dependent on a concentration of the substance absorbed by the sensitive material, wherein the sensitive layer extends on opposite sides of the plane, and respective capacitively coupled portions of the first electrode structure and of the second electrode structure are incorporated in the sensitive layer; and
   a structural layer having a cavity; wherein the first electrode structure and the second electrode structure are arranged on the structural layer and extend through the cavity and wherein the sensitive layer fills the cavity, wherein the structural layer comprises a plurality of cavities, that includes the cavity, separated by at least one wall and wherein the first electrode structure and the second electrode structure extend transversely to the at least one wall.

2. The sensor according to claim 1 wherein the sensitive layer extends between a first surface and a second surface and the first electrode structure and the second electrode structure are arranged between the first surface and the second surface.

3. The sensor according to claim 1, comprising a first supporting structure and a second supporting structure, defining a recess between each other; wherein the first electrode structure and the second electrode structure are arranged respectively on the first supporting structure and on the second supporting structure and wherein the sensitive layer fills the recess between the first supporting structure and the second supporting structure.

4. The sensor according to claim 1 wherein the first electrode structure and the second electrode structure comprise respectively a plurality of first fingers and a plurality of second fingers that extend along a first direction and are arranged alternated in succession along a second direction perpendicular to the first direction.

5. The sensor according to claim 4 wherein the first fingers and the second fingers have equal thickness and respective widths in the second direction and wherein adjacent first fingers and second fingers are separated by a uniform spacing.

6. The sensor according to claim 5 wherein the spacing, the thickness and the widths of the first fingers and of the second fingers are equal to one another.

7. The sensor according to claim 5 wherein the spacing, the thickness and the widths of the first fingers and of the second fingers are less than 1 m.

8. The sensor according to claim 5 wherein a portion of the sensitive layer comprised between the plane and the first surface and a second portion of the sensitive layer comprised between the plane and the second surface have respective thicknesses that are equal to or greater than the sum of the spacing and of the width of the first fingers or of the second fingers.

9. The sensor according to claim 1, comprising a heater in a region corresponding to the first electrode structure and to the second electrode structure.

10. The sensor according to claim 1 wherein the sensitive layer has a free surface exposed and accessible from outside.

11. The sensor according to claim 1 wherein the sensitive material is selected from the group consisting of: polyimide; polymethylmetacrilate; poly(2-hydroxyethylmethylmetacrilate); 94.5% polydimethylsiloxane copolymer, 5% diphenyl siloxane copolymer, 0.5% methyl-vinyl-siloxane; polyethylene-co-vinylacetate with 40% acetate content; polycarbonate urethane; and siloxane hexafluoro alcohol.

12. A process for manufacturing a sensor of substances, comprising:
    forming a structural layer having a plurality of cavities and at least one wall that separates the cavities from each other;
    forming a first electrode structure and a second electrode structure capacitively coupled, comb-fingered and arranged co-planar on a plane extending on a surface of the structural layer, the first electrode structure and the second electrode structure extending transversely to the at least one wall; and
    forming a sensitive layer on opposite sides of the plane, the sensitive layer being of a sensitive material that is permeable to a substance and has an electric permittivity dependent on a concentration of the substance absorbed by the sensitive material.

13. The process according to claim 12 wherein a first portion of the sensitive layer extends between a first surface and the plane and a second portion of the sensitive layer extends between the plane and a second surface, the first electrode structure and the second electrode structure are arranged between the first portion of the sensitive layer and the second portion of the sensitive layer.

14. The process according to claim 12 wherein forming the sensitive layer comprises encapsulating the first electrode structure and the second electrode structure inside the sensitive layer.

15. The process according to claim 14, wherein:
    at least one cavity of the plurality of cavities is in a region of the structural layer underlying the first electrode structure and the second electrode structure, so that comb-fingered portions of the first electrode structure and of the second electrode structure are suspended above the cavity with respective ends anchored to the structural layer; and
    forming the first sensitive layer comprises filling the at least one cavity with the sensitive material.

16. The process according to claim 12, comprising:
    selectively etching the structural layer, so as to form at least one of the plurality of cavities between the first electrode structure and the second electrode structure;
    and wherein forming the first sensitive layer includes filling the at least one cavity with the sensitive material.

17. A sensor, comprising:
    a structural layer having a first cavity, a second cavity, and a wall that separates the first cavity from the second cavity by a wall;
    a first electrode structure and a second electrode structure capacitively coupled, comb-fingered, and arranged co-planar on a plane, the first electrode structure and the second electrode structure being on, and extending transversely with respect to, the wall; and
    a sensitive layer of a sensitive material that is permeable to a substance and has electric permittivity dependent on a concentration of the substance absorbed by the sensitive material,
    wherein the sensitive layer extends on opposite sides of the plane and completely surrounds the first electrode structure and the second electrode structure where the first electrode structure and the second electrode structure are capacitively coupled together.

18. The sensor of claim 17, wherein the structural layer contacts first, second, and third sides of the sensitive layer, the sensitive layer being positioned in the first cavity and the second cavity.

19. The sensor of claim 17, wherein the sensitive layer includes a first portion and a second portion, the first electrode structure and the second electrode structure positioned between the first portion and the second portion.

* * * * *